US007662843B2

(12) United States Patent
Al-Abed

(10) Patent No.: US 7,662,843 B2
(45) Date of Patent: Feb. 16, 2010

(54) ISOXAZOLINE COMPOUNDS HAVING MIF ANTAGONIST ACTIVITY

(75) Inventor: Yousef Al-Abed, Locust Valley, NY (US)

(73) Assignee: Cytokine PharmaSciences, Inc., King of Prussia, PA (US)

( * ) Notice: Subject to any disclaimer, the term of this patent is extended or adjusted under 35 U.S.C. 154(b) by 848 days.

(21) Appl. No.: 10/828,240

(22) Filed: Apr. 21, 2004

(65) Prior Publication Data

US 2004/0204464 A1  Oct. 14, 2004

Related U.S. Application Data

(63) Continuation of application No. 10/164,630, filed on Jun. 10, 2002.

(60) Provisional application No. 60/296,478, filed on Jun. 8, 2001.

(51) Int. Cl.
*A01N 43/80* (2006.01)
*C07D 261/02* (2006.01)

(52) U.S. Cl. ..................... 514/378; 548/240

(58) Field of Classification Search .................. 514/378; 548/240
See application file for complete search history.

(56) References Cited

U.S. PATENT DOCUMENTS

| 4,933,464 | A | 6/1990 | Markofsky |
| 5,716,967 | A | 2/1998 | Kleinman |
| 5,849,736 | A | 12/1998 | Wityak et al. |
| 6,114,367 | A | 9/2000 | Cohan et al. |
| 6,599,903 | B2 | 7/2003 | de Lassauniere et al. |
| 6,630,461 | B2 | 10/2003 | de Lassauniere et al. |

OTHER PUBLICATIONS

Cvetkovic, I. and Stosic-Grujicic "Neutralization of mcrophage migration inhibitory factor-novel approach for the treatment of immunoinflammatory disorders" 2006, International Immunopharmocology, vol. 6, pp. 1527-1534.*
Swope, et al., "Macrophage Migration Inhibitory Factor: Cytokine, Hormone, or Enzyme?", Rev. Physiol. Bicohem. Pharmacol., 139, 1-32 (1999).
Metz, et al., "Role of Macrophage Migration Inhibitory Factor in the Regulation of the Immune Response", Adv. Immunol., 66, 197-223 (1997).
Bucala, "MIF Rediscovered: Cytokine, Pitutary Hormone, and Glucocorticoid-Induced Regulator of the Immune Response", FASEB J., 14, 1607-1613 (1996).
George, et al., "In vitro Cell Migration as a Model for Delayed Hypersensitivity", Proc. Soc. Exp. Biol. Med., 111, 514-521 (1962).
Weiser, et al., "Studies on Human Inhibitory Factor: Characterization of Three Molecular Species", J. Immunol., 126, 5, 1958-1962 (1981).
Bloom, et al., "Mechanism of a Reaction in Vitro Associated with Delayed-Type Hypersensitivity", Science, 153, 80-82 (1966).

David, "Delayed Hypersensitivity in Vitro: Its Mediation by Cell-Free Substances Formed by Lymphoid Cell-Antigen Interaction", Proc. Natl. Acad. Sci. USA, 56, 72-77 (1966).
Nathan, et al., "Characterization of a Lymphocyte Factor Which Alters Macrophage Functions", J. Exp. Med., 137, 275-288 (1973).
Nathan, et al., "Alterations of Macrophage Functions by Mediators from Lymphocytes", J. Exp. Med., 133, 1356-1376 (1971).
Churchill, et al., "Macrophages Activated as Suspension Cultures with Lymphocyte Mediators Devoid of Antigen Become Cytotoxic for Tumor Cells", J. Immunol., 115, 8, 781-785 (1975).
McInnes, et al., "Interleukin 4 Induces Cultured Monocytes/Macrophages to Form Giant Multinucleated Cells", J. Exp. Med., 167, 598-611 (1988).
Thurman, et al., "MIF-Like Activity of Natural and Recombinant Human Interferon-γ and Their Neutralization by Monoclonal Antibody", J. Immunol., 134, 1, 305-309 (1985).
Weiser, et al., "Molecular Cloning of a cDNA Encoding a Human Macrophage Migration Inhibitory Factor", Proc. Natl. Acad. Sci. USA, 86, 7522-7526 (1989).
Weiser, et al., "Human Recombinant Migration Inhibitory Factor Activates Human Macrophages to Kill *Leishmania donovani*", J. Immunol., 147, 6, 2006-2011(1991).
Pozzi, et al., "Human Recombinant Migration Inhibitory Factor Activates Human Macrophages to Kill Tumor Cells", Cellular Immunol., 145, 372-379 (1992).
Weiser, et al., "Recombinant Human Migration Inhibitory Factor Has Adjuvant Activity", Proc. Natl. Acad. Sci. USA, 89, 8049-8052 (1992).
Cunha, et al., "Recombinant Migration Inhibitory Factor Induces Nitric Oxide Synthase in Murine Macrophages", J. Immunol., 150, 5, 1908-1912 (1993).
Rice, et al., "Macrophage Migration Inhibitory Factor (MIF): A Critical Upstream Regulator of Acute and Chronic Inflammatory Responses", Chapter 24, Annual Reports in Medicinal Chemistry, 33, 243-252 (1998).
Donnelly, et al., "Macrophage Migration Inhibitory Factor: A Regulator of Glucocorticoid Activity with a Critical Role in Inflammatory Disease", Molecular Medicine Today, 3, 502-507 (1997).
Bacher, et al., "An Essential Regulatory Role for Macrophage Migration Inhibitory Factor in T-Cell Activation", Proc. Natl. Acad. Sci. USA, 93, 7849-7854 (1996).

(Continued)

*Primary Examiner*—Sreeni Padmanabhan
*Assistant Examiner*—Kendra D Carter
(74) *Attorney, Agent, or Firm*—John K. Pike; Law Office of John K. Pike, PLLC

(57) ABSTRACT

Methods of use and pharmaceutical compositions for a genus of low molecular weight compounds comprising optionally substituted isoxazoline ring systems that act as inhibitors of MIF (macrophage migration inhibitory factor) are disclosed. Specifically, the compounds are useful for treating a variety of diseases involving inflammatory activity or pro-inflammatory cytokine responses, such as autoimmune diseases (including rheumatiod arthritis, insulin-dependent diabetes, multiple sclerosis, graft versus host disease, lupus syndromes), asthma, arthritis, ARDS, psoriasis, interleukin-2 toxicity, proliferative vascular disease, and various forms of sepsis and septic shock, and other conditions characterized by underlying MIF responses including, for instance, tumor growth and neovascularization (angiogenesis).

5 Claims, 5 Drawing Sheets

OTHER PUBLICATIONS

Mikayama, et al., "Molecular Cloning and Functional Expression of a cDNA Encoding Glycosylation-Inhibiting Factor", Proc. Natl. Acad. Sci. USA, 90, 10056-10060 (1993).

Hudson, et al., "A Proinflammatory Cytokine Inhibits p53 Tumor Suppressor Activity", J. Exp. Med., 190, 10, 1375-1382 (1999).

Sakaue, et al., "Regulation of Macrophage Migration Inhibitory Factor (MIF) Expression by Glucose and Insulin in Adipocytes In Vitro", Mol. Med., 5, 361-371 (1999).

Chesney, et al., "An Essential Role for Macrophage Migration Inhibitory Factor (MIF) in Angiogenesis and the Growth of a Murine Lymphoma", Mol. Med., 5, 181-191 (1999).

Shimizu, et al., "High Expression of Macrophage Migration Inhibitory Factor in Human Melanoma Cells and Its Role in Tumor Cell Growth and Angiogenesis", Biochem. and Biophys. Res. Commun. 264, 751-758 (1999).

Rosengren, et al., "The Immunoregulatory Mediator Macrophage Migration Inhibitory Factor (MIF) Catalyzes a Tautomerization Reaction", Mol. Med., 2, 1, 143-149 (1996).

Bendrat, et al., "Biochemical and Mutational Investigations of the Enzymatic Activity of Macrophage Migration Inhibitory Factor", Biochemistry, 36, 15356-15362 (1997).

Rosengren, et al., "The Macrophage Migration Inhibitory Factor MIF is a Phenylpyruvate Tautomerase", FEBS Letters, 417, 85-88 (1997).

Matsunaga, et al., "Enzyme Activity of Macrophage Migration Inhibitory Factor Toward Oxidized Catecholamines", J. Biol. Chem., 274, 6, 3268-3271 (1999).

Lolis, et al., "Crystal Structure of Macrophage Migration Inhibitory Factor (MIF), a Glucocorticoid-Induced Regulator of Cytokine Production, Reveals a Unique Architecture", Proc. Ass. Am. Phys., 108, 6, 415-419 (1996).

Swope, et al., "Direct Link Between Cytokine Activity and a Catalytic Site for Macrophage Migration Inhibitory Factor", EMBO, 17, 13, 3534-3541 (1998).

Sugimoto, et al., "Crystal Structure of Human D-Dopachrome Tautomerase, a Homologue of Macrophage Migration Inhibitory Factor, at 1.54 Å Resolution", Biochemistry, 38, 3268-3279 (1999).

Lubetsky, et al., "Pro-1 of Macrophage Migration Inhibitory Factor Functions as a Catalytic Base in the Phenylpyruvate Tautomerase Activity", Biochemistry, 38, 7346-7354 (1999).

Taylor, et al., "Crystal Structure of Macrophage Migration Inhibitory Factor Complexed with (E)-2-Fluoro-p-hydroxycinnamae at 1.8 Å Resolution: Implications for Enzymatic Catalysis and Inhibition", Biochemistry, 38, 7444-7452 (1999).

Hermanowski-Vosatka, et al., "Enzymatically Inactive Macrophage Migration Inhibitory Factor Inhibits Monocyte Chemotaxis and Randome Migration", Biochemistry, 38, 12841-12849 (1999).

Bernhagen, et al., "MIF is a Pituitary-Derived Cytokine that Potentiates Lethal Endotoxaemia", Nature, 365, 756-759 (1993).

Kobayashi, et al., "Prevention of Lethal Acute Hepatic Failure by Antimacrophage Migration Inhibitory Factor Antibody in Mice Treated with Bacille Calmette-Guerin and Lipopolysaccharide", Hepatology, 29, 1752-1759 (1999).

Calandra, et al., "Macrophage Migration Inhibitory Factor is a Critical Mediator of the Activation of Immune Cells by Exotoxins of Gram-Positive Bacteria", Proc. Natl. Acad. Sci. USA, 95, 11383-11388 (1998).

Makita, et al., "Effect of Anti-Macrophage Migration Inhibitory Factor Antibody on Lipopolysaccharide-Induced Pulmonary Neutrophil Accumulation", Am. J. Respir. Crit. Care Med., 158, 573-579 (1998).

Bacher, et al., "An Essential Regulatory Role for Macrophage Migration Inhibitory Factor in T-Cell Activation", Proc. Natl. Acad. Sci. USA, 93, 7849-7854 (1996).

Kitaichi, et al., "Inhibition of Experimental Autoimmune Uveoretinitis with Anti-Macrohage Migration Inhibitory Factor Antibodies", Curr. Eye Res. 20, 2, 109-114 (2000).

Leech, et al., "Macrophage Migration Inhibitory Factor in Rheumatoid Arthritis", Arthritis & Rheum., 42, 8, 1601-1608 (1999).

Curuzu, et al., "Reaction of 4-Aroly-2(3H)-Dihydrofuranones with Hydroxylamine Hydrochloride. Synthesis and Pharmacological Study of a Series of 3-Aryl-4,5-Dihydro-4-Isoxazoleacetic Acids", Collect. Czech. Chem. Commun., 56, 2494-2499 (1991).

Wityak, et al., "Discovery of Potent Isoxazoline Glycoprotein IIb/IIIa Receptor Antagonists", J. Med. Chem., 40, 50-60 (1997).

Eichenger, et al., "A Convenient Synthesis of 3- And 3,4-Substituted 4,5-Dihydroisoxazole-5-Acetic Acids", Synth. Commun., 27, 16, 2733-2742 (1997).

Eicheinger, et al., "A Novel Base Promoted Reaction of Methyl 2-Isoxazoline-5-Acetates to 5-(2-Oxoethyl)-3-Isoxazolidinones", Synth. Commun., 28, 13, 2457-2466 (1998).

Kleinman, et al., "Striking Effect on Hydroxamic Acid Substitution on the Phosphodiesterase Type 4 (PDE4) and TNFα Inhibitory Activity of Two Series of Rolipram Analogues: Implications for New Active Site Model of PDE4", J. Med. Chem. 41, 266-270 (1998).

Donnelly, et al., "Regulatory Role for Macrophage Migration Inhibitory Factor in Acute Respiratory Distress Syndrome", Nat. Med. 3, 3, 320-323 (1997).

Leech, et al., "Involvement of Macrophage Migration Inhibitory Factor in the Evolution of Rat Adjuvant Arthritis", Arthritis & Rheum., 41, 5, 910-917 (1998).

Onodera, et al., "High Expression of Macrophage Migration Inhibitory Factor in the Synovial Tissues of Rheumatoid Joints", Cytokine, 11, 2, 163-167 (1999).

Mikulowska, et al., "Macrophage Migration Inhibitory Factor is Involved in the Pathogenesis of Collagen Type II-Induced Arthritis in Mice", J. Immunol. 158, 5514-5517 (1997).

Shimizu, et al., "Identification of Macrophage Migration Inhibitory Factor (MIF) in Human Skin and Its Immunohistochemical Localization", FEBS Lett., 381, 199-202 (1996).

Takahashi, et al., "Involvement of Macrophage Migration Inhibitory Factor (MIF) in the Mechanism of Tumor Cell Growth", Mol. Med., 4, 707-714 (1998).

Bozza, et al., "Targeted Disruption of Migration Inhibitory Factor Gene Reveals Its Critical Role in Sepsis", J. Exp. Med., 189, 2, 341-346 (1999).

Fingl, et al., "Introduction: General Principles", The Pharmacological Basis of Therapeutics, Chapter 1, 1-46 (1975).

Xue, et al., "Discovery of an Orally Active Series of Isoxazoline Glycoprotein IIb/IIIa Antagonists", J. Med. Chem., 40, 2064-2084 (1997).

Baraldi, et al., "Nitrile Oxide [3+2] Cycloaddition: Application to the Synthesis of 6-Substituted 3(2H)-Pyridazinones and 6-Substituted 4,5-Dihydro-4-Hydroxy-3(2H)-Pyridazinones", Synthesis-Stuttgart—1994, 11, 1158-1162 (1994).

Bernhagan, et al., "Purification, Bioactivity, and Secondary Structure Analysis of Mouse and Human Macrophage Migration Inhibitory Factor (MIF)", Biochemistry, 33, 14144-14155 (1994).

Supplementary Partial European Search Report, European Patent Application No. 02741873, dated Feb. 23, 2007.

Curzu, M.M., et al., "Reaction of 4-Aroyl-2(3H)-Dihydrofuranones with Hydroxylamine Hydrochloride Synthesis and Pharmacological Study of a Series of 3-Aryl-4,5-Dihydro-4-Isoxazoleacetic Acids," Collect. Czech. Chem. Commun., 56:2494-2499, (1991).

Eichinger, K., et al., "A Convenient Synthesis of 3- and 3,4-Substituted 4,5-Dihydroisoxazole-5-Acetic Acids," Synthetic Communications, 27(16):2733-2742, (1997).

Lubetsky, J.B., et al., "The Tautomerase Activity Site of Macrophage Migration Inhibitory Factor is a Potential Target for Discovery of Novel Anti-Inflammatory Agents," The Journal of Biological Chemistry, 277(28):24976-24982, (Jul. 12, 2002).

* cited by examiner

Synthesis of p-hydroxyphenyl-isoxazoline methyl ester

Figure: Synthesis of (R,S)-3-(4-hydroxyphenyl)-4,5-dihydro-5-isoxazoleacetic acid methyl ester.

Compound 4 inhibits MIF glucocorticoid regulating activity

Modification of isoxazoline (4)

Retrosynthetic approach to ISO-2

Synthesis of functionalized isoxazoline derivatives

ISOXAZOLINE COMPOUNDS HAVING MIF ANTAGONIST ACTIVITY

This application is a continuation of U.S. patent application Ser. No. 10/164,630, filed Jun. 10, 2002, currently pending, which claims priority from U.S. Provisional Application Ser. No. 60/296,478, filed Jun. 8, 2001, each of which are hereby incorporated by reference in their entirety.

BACKGROUND OF THE INVENTION

1. Field of the Invention

The present invention provides a genus of optionally substituted isoxazoline compounds and related methods of use and pharmaceutical compositions. The compounds have MIF (macrophage migration inhibitory factor) antagonist activity. Specifically, the MIF antagonists are useful in methods for treating a variety of diseases involving inflammatory activity or pro-inflammatory cytokine responses, such as autoimmune diseases, asthma, arthritis, multiple sclerosis, ARDS (acute respiratory distress syndrome) and various forms of sepsis and septic shock, and other conditions characterized by underlying MIF responses including, for instance, tumor growth and neovascularization.

2. Background of the Technology

Macrophage migration inhibitory factor (MIF) is one of the earliest described cytokines, and is an immunoregulatory protein with a wide variety of cellular and biological activities (for reviews see: Swope, et al., Rev. Physiol. Biochem. Pharmacol. 139,1-32 (1999); Metz et al., Adv. Immunol. 66,197-223 (1997); and Bucala, FASEB J. 14, 1607-1613 (1996)). Originally, MIF was found to be secreted by activated lymphoid cells, to inhibit the random migration of macrophages, and to be associated with delayed-type hypersensitivity reactions (George et al., Proc. Soc. Exp. Biol. Med., 111, 514-521 (1962); Weiser, et al., J. Immunol. 126, 1958-1962 (1981); Bloom et al., Science, 153:80-82 (1966); David, Proc. Natl. Acad. Sci. USA, 56, 72-77 (1966). MIF was also shown to enhance macrophage adherence, phagocytosis and tumoricidal activity (Nathan et al., J. Exp. Med., 137, 275-288 (1973); Nathan, et al., J. Exp. Med., 133, 1356-1376 (1971); Churchill et al., J. Immunol., 115, 781-785 (1975)). Unfortunately, many of the early MIF studies used mixed-culture supernatants that were shown later to contain other cytokines, such as IFN-γ and IL-4, that also have macrophage migration inhibitory activity (McInnes et al., J. Exp. Med., 167, 598-611 (1988); Thurman, et al., J. Immunol., 134, 305-309 (1985)). The availability of recombinant MIF has allowed for confirmation of these biological activities, and for the identification of additional activities.

Recombinant human MIF was originally cloned from a human T cell library (Weiser et al., Proc. Natl. Acad. Sci. USA, 86, 7522-7526 (1989)), and was shown to activate blood-derived macrophages to kill intracellular parasites and tumor cells in vitro, to stimulate IL-1β and TNFα expression, and to induce nitric oxide synthesis (Weiser, et al., J. Immunol., 147, 2006-2011 (1991); Pozzi, et al., Cellular Immunol., 145, 372-379 (1992); Weiser, et al., Proc. Natl. Acad. Sci. USA, 89, 8049-8052 (1992); Cunha, et al., J. Immunol., 150, 1908-1912 (1993)). While the conclusions available from several of these early reports are confounded by the presence of a bioactive mitogenic contaminant in the recombinant MIF preparations used, the potent pro-inflammatory activities of MIF have been established in other studies that do not suffer from this complicating factor (reviewed in Bucala, The FASEB, Journal 10,1607-1613 (1996)).

More recent MIF studies have capitalized on the production of recombinant MIF in purified form as well as the development of MIF-specific polyclonal and monoclonal antibodies to establish the biological role of MIF in a variety of normal homeostatic and pathophysiological settings (reviewed in Rice, et al., Annual Reports in Medicinal Chemistry, 33, 243-252 (1998)). Among the most important insights of these later reports has been the recognition that MIF not only is a cytokine product of the immune system, but also is a hormone-like product of the endocrine system, particularly the pituitary gland. This work has underscored the potent activity of MIF as a counter-regulator of the anti-inflammatory effects of the glucocorticoids (both those endogenously released and those therapeutically administered), with the effect that the normal activities of glucocorticoids to limit and suppress the severity of inflammatory responses are inhibited by MIF. The endogenous MIF response is thus seen as a cause or an exacerbative factor in a variety of inflammatory diseases and conditions (reviewed in Donnelly, et al., Molecular Medicine Today, 3, 502-507 (1997)).

MIF is now known to have several biological functions beyond its well-known association with delayed-type hypersensitivity reactions. For example, as mentioned above, MIF released by macrophages and T cells acts as a pituitary mediator in response to physiological concentrations of glucocorticoids (Bucala, FASEB J., 14, 1607-1613 (1996)). This leads to an overriding effect of glucocoticoid immunosuppressive activity through alterations in TNF-α, IL-1β, IL-6, and IL-8 levels. Additional biological activities of MIF include the regulation of stimulated T cells (Bacher et al., Proc. Natl. Acad. Sci. USA, 93, 7849-7854 (1996)), the control of IgE synthesis (Mikayama, et al., Proc. Natl. Acad. Sci. USA, 90, 10056-10060 (1993)), the functional inactivation of the p53 tumor suppressor protein (Hudson et al., J. Exp. Med., 190, 1375-1382 (1999)), the regulation of glucose and carbohydrate metabolism (Sakaue et al., Mol. Med., 5, 361-371 (1999)), and the attenuation of tumor cell growth and tumor angiogenesis (Chesney et al., Mol. Med., 5, 181-191 (1999); Shimizu, et al., Biochem. Biophys. Res. Commun., 264, 751-758 (1999)).

MIF shares significant sequence homology (36% identity) with D-dopachrome tautomerase. This led to the discovery that MIF has enzymatic activity and catalyzes the tautomerization of the non-physiological substrates D-dopachrome (Rosengren et al., Mol. Med., 2,143-149 (1996)) and L-dopachrome methyl ester (Bendrat et al., Biochemistry, 36, 15356-15362 (1997). Additionally, phenylpyruvic acid and p-hydroxyphenylpyruvic acid (Rosengren, et al., FEBS Letter, 417, 85-88 (1997)), and 3,4-dihydroxyphenylaminechrome and norepinephrinechrome (Matsunaga et al., J. Biol. Chem., 274, 3268-3271 (1999), are MIF substrates, although it is not known if tautomerization of any of these agents comprises a natural function for MIF.

The three-dimensional crystal structure of human MIF reveals that the protein exists as a homotrimer (Lolis, et al., Proc. Ass. Am. Phys., 108, 415-419 (1996) and is structurally related to 4-oxalocrotonate tautomerase, 5-carboxymethyl-2-hydroxymuconate, chorismate mutase, and to D-dopachrome tautomerase (Swope, et al., EMBO J., 17, 3534-3541 (1998); Sugimoto, et al., Biochemistry, 38, 3268-3279 (1999). Recently, the crystal structure has been reported for the complex formed between human MIF and p-hydroxyphenylpyruvic acid (Lubetsky, et al., Biochemistry, 38, 7346-7354 (1999). It was found that the substrate binds to a hydrophobic cavity at the amino terminus and interacts with Pro-1, Lys-32, and Ile-64 in one of the subunits, and with Tyr-95 and Asn-97 in an adjacent subunit. Similar interactions between murine MIF and (E)-2-fluoro-p-hydroxycinnamate have been reported (Taylor, et al., Biochemistry, 38, 7444-7452 (1999)). Solution studies using NMR provide further evidence of the interaction between p-hydroxyphenylpyruvic acid and Pro-1 in the amino-terminal hydrophobic cavity (Swope, et al., EMBO J., 17, 3534-3541 (1998)).

Mutation studies provide convincing evidence that Pro-1 is involved in the catalytic function of MIF. Deletion of Pro-1 or replacement of Pro-1 with Ser (Bendrat, et al., Biochemistry, 36,15356-15362 (1997)), Gly (Swope, et al., EMBO J., 17, 3534-3541 (1998)), or Phe (Hermanowski-Vosatka, et al., Biochemistry, 38, 12841-12849 (1999)), and addition of an N-terminal peptide tag to Pro-1 (Bendrat, et al., Biochemistry, 36, 15356-15362 (1997)) abrogated the catalytic activity of MIF in assays using L-dopachrome methyl ester and p-hydroxyphenylpyruvic acid. A similar loss in activity was found by inserting Ala between Pro-1 and Met-2 (Lubetsky et al., Biochemistry, 38,7346-7354 (1999). The connection between the enzymatic and biological activities, however, remains unclear. The Pro to Ser MIF mutant showed glucocorticoid counter-regulatory activity (Bendrat, et al., Biochemistry, 36,15356-15362 (1997)) and was fully capable, as was the Pro to Phe mutant, of inhibiting monocyte chemotaxis (Hermanowski-Vosatka et al., Biochemistry, 38, 12841-12849 (1999). In contrast, the Pro to Gly MIF mutant was greatly impaired in its ability to stimulate superoxide generation in activated neutrophils (Swope et al., EMBO J., 17, 3534-3541 (1998). These results suggest that the biological activity of enzymatically inactive MIF mutants may be dependent not only on the nature of the mutation, but also on the assay that is used to assess biological function.

There is a need in the art to discover and develop small organic molecules that function as MIF inhibitors (e.g., antagonists) and further posses the benefits of small organic molecule therapeutics versus larger, polymeric protein (e.g., antibody) and nucleic acid-based (e.g., anti-sense) therapeutic agents. The therapeutic potential of low molecular weight MIF inhibitors is substantial, given the activities of anti-MIF antibodies in models of endotoxin- and exotoxin-induced toxic shock (Bernhagen et al., Nature, 365, 756-759 (1993); Kobayashi et al., Hepatology, 29,1752-1759 (1999); Calandra et al., Proc. Natl. Acad. Sci. USA., 95, 11383-11388 (1998); and Makita et al., Am. J. Respir. Crit. Care Med. 158, 573-579 (1998), T-cell activation (Bacher et al., Proc. Natl. Acad. Sci. USA., 93, 7849-7854 (1996), autoimmune diseases (e.g., graft versus host disease, insulin-dependent diabetes, and various forms of lupus) including rheumatoid arthritis (Kitaichi, et al., Curr. Eye Res., 20, 109-114 (2000); Leech, et al., Arthritis Rheum., 42, 1601-1608 (1999), wound healing (Abe, et al., Biochim. Biophys. Acta, 1500, 1-9 (2000), and angiogenesis (Shimizum, et al., Biochem. Biophys. Res. Commun., 264, 751-758 (1999). Low molecular weight anti-MIF drugs exhibiting such activities may offer clinical advantages over neutralizing antibodies and nucleic acid-based agents because they may be orally active or generally more easily administered, have better bioavailabilities, have improved biodistributions, and should be much cheaper to produce. Prior to the present invention, the only published report of potent low molecular weight MIF inhibitors concerned some commonly found long chain fatty acids that reversibly inhibited the dopachrome tautomerase activity of mouse MIF (Bendrat et al., Biochemistry, 36, 15356-15362 (1997). These fatty acids were never tested for their effects in biological assays of MIF activity.

U.S. Pat. No. 4,933,464 to Markofsky discloses a process for forming 3-phenylisoxazolines and 3-phenylisoxazoles and related products.

U.S. Pat. No. 6,114,367 to Cohan et al. discloses isoxazoline compounds which are inhibitors of tumor necrosis factor (TNF). The isoxazoline compounds are said to be useful for inhibiting TNF in a mammal in need thereof and in the treatment or alleviation of inflammatory conditions or disease. Also disclosed are pharmaceutical compositions comprising such compounds.

Curuzu et al., Collect. Czech. Chem. Commun., 56: 2494-2499 (1991) discloses 3-substituted phenyl-4,5-dihydroisoxazoleneacetic acids, including 3-(4-hydroxyphenyl)-4,5-dihydro-5-isoxazolineacetic acid and 3-(4-methoxyphenyl)-4,5-dihydro-5-isoxazolineacetic acid, and shows that the first of these two compounds is devoid of antiinflammatory activity, while the second is dramatically reduced in such activity compared to the parent compound that was unsubstituted in the para position of the phenyl ring, in a carageenin-induced edema assay in the rat paw.

Wityak et al., J. Med. Chem., 40: 50-60 (1997) discloses isoxazoline antagonists of the glycoprotein IIb/IIIa receptor.

Eichenger, et al., Synth. Commun. 27 (16): 2733-2742 (1997) discloses [3-(4-methoxy-phenyl)-4,5-dihydro-isoxazol-5-yl]-acetic acid.

Eichinger, et al., Synth. Commun. 28(13): 2457-2466 (1998) discloses [3-(4-methoxy-phenyl)-4,5-dihydro-isoxazol-5-yl]-acetic acid and the methyl ester thereof.

Kleinman et al., "Striking effect of hydroxamic acid substitution on the phosphodiesterase type 4 (PDE4) and TNF alpha inhibitory activity of two series of rolipram analogues: implications for a new active site model of PDE4". J. Med. Chem. 41(3): 266-270 (1998), discloses inter alia the following compounds: [3-(3-cyclopentyloxy-4-methoxy-phenyl)-4,5-dihydro-isoxazol-5-yl]-acetic acid and the methyl ester thereof, as well as [3-(3-cyclopentyloxy-4-methoxy-phenyl)-4,5-dihydro-isoxazol-5-yl]-N-hydroxy-acetamide.

U.S. application Ser. No. 09/625,829, filed Jul. 26, 2000, which is hereby incorporated herein by reference in its entirety, discloses quinone-related compounds having MIF inhibitor activity. U.S. application Ser. No. 09/699,258, filed Oct. 27, 2000, which is hereby incorporated herein by reference in its entirety, discloses amino acid/benzaldehyde Schiff base compounds having MIF inhibitor activity.

SUMMARY OF THE INVENTION

The enzyme activity (tautomerase) of MIF and the substrates it accepts provide an enzymatic activity assay for designing low molecular weight agents that bind to MIF and disrupt its biological activity. The present invention provides methods of use for a genus of such compounds having isoxazoline structures.

The present invention provides a method for treating inflammatory disorders including, but not limited to, arthritis, proliferative vascular disease, ARDS (acute respiratory distress syndrome), cytokine-mediated toxicity, sepsis, septic shock, psoriasis, interleukin-2 toxicity, asthma, MIF-mediated conditions, autoimmune disorders (including but not limited to, rheumatoid arthritis, insulin-dependent diabetes, multiple sclerosis, graft versus host disease, lupus syndromes), tumor growth or angiogenesis, or any condition characterized by local or systemic MIF release or synthesis, comprising administering an effective amount of a compound of Formula I, wherein Formula I is:

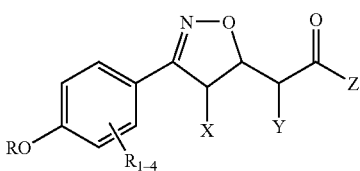

wherein:
  $R_{1-4}$ are, independently, R, halo, $N_3$, CN, OH, NRR', or SH;
  R and R' are, independently, H or $C_{1-6}$ alkyl;
  X is R, halo, $N_3$, CN, OR, NRR', SH, =O, =$CH_2$, or A;
  A is a substituted or unsubstituted aromatic ring;
  Y is R, NRR', NRR" or $(CH_2)_n$-A;
  Z is R, OR, OR", NRR', NRR", or A;
  R" is a saturated or unsaturated, straight or branched chain $C_2$-$C_{18}$;
  and n is 0 or 1.

Preferably, the compound is a p-hydroxyphenyl-isoxazoline-containing compound, wherein each of R, $R_{1-4}$, X and Y is H or —$CH_2$-A, and Z is OR. More preferably, the compound is an ester of (R)-3-(4-hydroxyphenyl)-4,5-dihydro-5-isoxazolineacetic, particularly the acid methyl ester thereof (identified as "ISO-1" herein) which is also known as, p-hydroxyphenol-isoxazoline methyl ester. Still more preferably the compound is an ester of 2-[3-(4-hydroxy-phenyl)-4,5-dihydro-isoxazol-5-yl]-3-phenyl-propanoic acid, particularly the methyl ester thereof (identified as "ISO-2").

The present invention further provides a pharmaceutical composition comprising a compound having an isoxazoline moiety, or a pharmaceutically acceptable salt thereof, and a pharmaceutically acceptable carrier or diluant, wherein the composition comprises an effective amount of a compound of Formula I, wherein Formula I is:

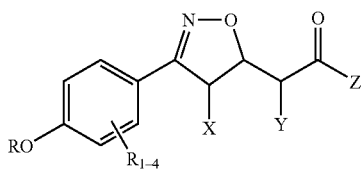

wherein:
  $R_{1-4}$ are, independently, R, halo, $N_3$, CN, OH, NRR', or SH;
  R and R' are, independently, H or $C_{1-6}$ alkyl;
  X is R, halo, $N_3$, CN, OR, NRR', SH, =O, =$CH_2$, or A;
  A is a substituted or unsubstituted aromatic ring;
  Y is R, NRR', NRR" or $(CH_2)_n$-A;
  Z is R, OR, OR", NRR', NRR', or A;
  R" is a saturated or unsaturated, straight or branched chain $C_2$-$C_{18}$;
  and n is 0 or 1.

with any or all of the following provisos:
(i) when Z=$OCH_3$, at least one of R, $R_{1-4}$, X and Y is not H;
(ii) when $R_1$=$R_2$=tert-butyl and each is ortho to OR, at least one of R, $R_3$, $R_4$, X and Y is not H or Z is not $OCH_3$;
(iii) when Z=OH and R=H or methyl, at least one of $R_4$, X and Y is not H (i.e., the compound is not [3-(4-hydroxy-phenyl)-4,5-dihydro-isoxazol-5-yl]-acetic acid or [3-(4-methoxy-phenyl)-4,5-dihydro-isoxazol-5-yl]-acetic acid ); and
(iv) when Z=$OCH_3$, and R=methyl, at least one of $R_{1-4}$, X and Y is not H (i.e., the compound is not [3-(4-methoxy-phenyl)-4,5-dihydro-isoxazol-5-yl]-acetic acid methyl ester).

The present invention also provides a pharmaceutical composition comprising a compound having an isoxazoline moiety, and a pharmaceutically acceptable carrier, wherein the compound forms a stable interaction with at least one amino acid residue of an MIF protein. Preferably, the interaction occurs at or near the active site of the tautomease activity of the MIF protein. Preferably, the compound is a hydroxyphenyl-isoxazoline-containing compound. More preferably, the compound is an ester of (R)-3-(4-hydroxyphenyl)-4,5-dihydro-5-isoxazolineacetic acid, particularly the methyl ester (ISO-1). Still more preferably the compound is and ester of 2-[3-(4-hydroxy-phenyl)-4,5-dihydro-isoxazol-5-yl]-3-phenyl-propanoic acid, particularly the methyl ester (ISO-2).

The present invention provides a method for treating inflammatory disorders (including, but not limited to, arthritis, proliferative vascular disease, ARDS (acute respiratory distress syndrome), cytokine-mediated toxicity, sepsis, septic shock, psoriasis, interleukin-2 toxicity, asthma, MIF-mediated conditions, autoimmune disorders (including but not limited to, rheumatoid arthritis, insulin-dependent diabetes, multiple sclerosis, graft versus host disease, lupus syndromes), tumor growth or angiogenesis, or any condition characterized by local or systemic MIF release or synthesis, comprising administering an effective amount of a compound having a isoxazoline moiety, wherein the compound forms a stable interaction with MIF protein. Preferably, the compound is a isoxazoline-containing compound or an hydroxyphenyl-isoxazoline -containing compound. More preferably, the compound is an ester of (R)-3-(4-hydroxyphenyl)-4,5-dihydro-5-isoxazolineacetic acid, particularly the methyl ester (ISO-1). Still more preferably the compound is and ester of 2-[3-(4-hydroxy-phenyl)-4,5-dihydro-isoxazol-5-yl]-3-phenyl-propanoic acid, particularly the methyl ester (ISO-2).

In accordance with the activity of MIF to interfere with the anti-inflammatory effects of steroids (such as the anti-inflammatory glucocorticoids), the compounds of Formula I find further utility to enhance the activity and therapeutic benefits of both endogenously arising and exogenously administered steroidal anti-inflammatory agents. Such benefits may, in some cases, be most evident by a reduced need for steroid therapy (e.g., lower dose amount or frequency; less potent agent; reduced need for systemic administration) or by reduced side-effects associated with steroid administration. The benefits of administering an MIF inhibitor (and specifically a compound of Formula I) may be realized as a monotherapy, using only the MIF inhibitor of the present invention, or as a combination therapy with additional anti-inflammatory agents, including especially, but without limitation, an anti-inflammatory steroid. Such combination therapy may be achieved through administration of a single formulation or pharmaceutical composition that combines the MIF inhibitor (particularly an inhibitor of Formula I) with at least one other anti-inflammatory agent (which may be a steroidal or a non-steroidal anti-inflammatory agent), or through administration of separate formulations or pharmaceutical compositions in conjunction with each other, or both.

DESCRIPTION OF THE INVENTION

Figure 1:
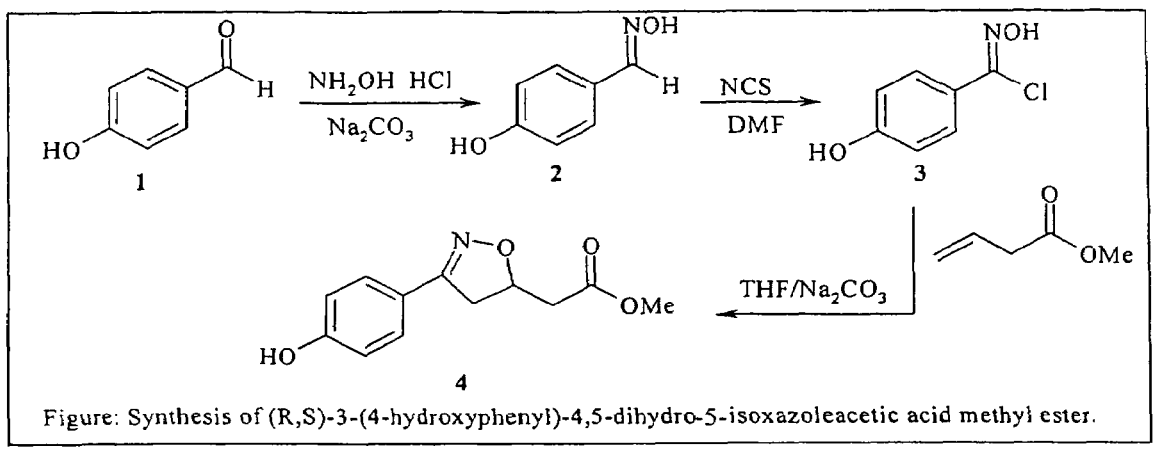
FIG. 1 shows the synthesis of p-hydroxyphenyl-isoxazoline methyl ester.

Based on structural similarities to amino acid Schiff base-type compounds described previously (see U.S. application Ser. No. 09/699,258, supra), the present inventors explored additional phenylimine scaffolds as pharmacophores for potential MIF antagonists. Several representative phenylimine compounds were synthesized and tested as inhibitors of the dopachrome tautomerase activity of MIF, and it was concluded that the isoxazolines represented an attractive scaffold for further attention. Thus, (S,R)-3-(4-hydroxyphenyl)-4,5-dihydro-5-isoxazole-acetic acid methyl ester presents certain structural elements that appeared to be important for binding to the MIF tautomerase active site, based on previous analysis by the inventors of phenylpyruvate:MIF co-crystalization and SAR results with the amino acid/benzaldehyde Schiff base type compounds U.S. application Ser. No. 09/699,258 (e.g., p-hydroxylated phenyl scaffold bearing an imine bond with an associated distal ester function).

Accordingly, the present invention provides a new class of potential MIF inhibitors related to isoxazoline which, unlike quinone-related inhibitors previously disclosed (U.S. application Ser. No. 09/699,258), may be suitable to neutralize both endogenous and exogenous MIF. In particular, isoxazoline was found as a racemic mixture to inhibit both MIF tautomerase and immunoregulatory activities with an $IC_{50}$ of 5.0 micromolar. Analysis of the co-crystal of MIF and isoxazoline 4 revealed the binding of only the S-enantiomer.

The present invention therefore provides a genus of MIF inhibitor compounds. Compounds in this genus are identified as MIF inhibitors because they inhibit MIF enzymatic activity in vitro. MIF catalyzes the tautomerization of a dopachrome-related MIF substrate to a colorless product. Unless specifically indicated to the contrary, references made herein to an inhibitory concentration (e.g., $IC_{50}$ or other activity index) refer to the inhibitory activity of a test compound in an MIF tautomerase assay (as further described in detail below, and in Bendrat, et al., Biochemistry, 36, 15356-15362 (1997).

MIF Tautomerase Activity

MIF catalyzes a tautomerization (i.e., keto-enol isomerization) reaction (Rosengren, et al., Molecular Medicine, 2, 143-149 (1996). The most active substrate identified is a non-physiological D-isomer of dopachrome. This reaction predicts therapeutic MIF inhibitors (see pending U.S. application Ser. No. 08/602,929, filed Feb. 16, 1996, and U.S. application Ser. No. 09/699,258, filed Oct. 27, 2000, the disclosures of which are incorporated herein by reference in their entirety). Inhibition of MIF tautomerase activity is predictive of inhibition of MIF biological activity.

A method for performing an assay for MIF dopachrome tautomerase activity begins with the preparation and oxidation of a DOPA-related substrate precursor, such as L-3,4-dihydroxyphenylalanine methyl ester. This oxidation with sodium periodate generates the corresponding dopachrome derivative (e.g., L-3,5-dihydro-6-hydroxy-5-oxo-2H-indole-2-carboxylic acid methyl ester ("dopachrome methyl ester") that is orange-colored and comprises a convenient substrate for use in a photometric assay for the enzymatic activity of MIF as a tautomerase. MIF (typically a purified preparation of recombinant MIF at a final concentration of 50-1000 ng/ml) addition causes the rapid tautomerization of the colored dopachrome substrate to a colorless 5,6-dihydroxyindole-2-caboxylic acid methyl ester product. The enzymatic activity of MIF is measured as the rate of de-colorization of the colored solution of the dopachrome-related substrate in a suitable buffer, typically at a time 20 seconds after addition of the final assay component and mixing. The absorbance is measured at about 475 nm (or 550 nm for substrate concentrations in excess 0.5 nM). A test compound may be included in the assay solution such that the effect of the test compound on MIF tautomerase activity (i.e., as an inhibitor) may be measured by noting the change in kinetics of substrate tautomerization compared to control assays performed in the absence of the test inhibitor compound. In particular, the MIF tautomerase assay may be conducted essentially as follows:

L-3,4-dihydroxyphenylalanine methyl ester (e.g., Sigma D-1507) is a dopachrome substrate precursor, and is prepared as a 4 mM solution in dd $H_2O$. Sodium periodate is prepared as an 8 mM solution in dd $H_2O$. Assay Buffer (50 mM potassium phosphate/1 mM EDTA, pH 6.0) is prepared. Purified recombinant MIF is prepared in 150 mM NaCl/20 mM Tris buffer (pH 7.4) as a stock solution convenient to supply MIF at a final concentration of about 700 ng/ml. Immediately prior to initiating the assay, 3.6 ml dopachrome substrate precursor solution, 2.4 ml periodate solution and 4.0 ml Assay Buffer are combined into a homogeneous mixture (this preparation of dopachrome substrate is suitable for assay use after 1 min and for about 30 min thereafter). Test compound (typically prepared as a concentrated stock in DMSO) and MIF are then combined with 0.7 ml Assay Buffer plus 0.3 ml dopachrome substrate solution to provide the desired final concentration of the test compound in a homogeneous mixture, and the optical density (absorbance) of this assay mixture is monitored at 475 nm. Typically, $OD_{475}$ is recorded every 5 sec for 0-60 sec, and the $OD_{475}$ for a given time point is compared to parallel assays where MIF is not added or the test compound is omitted. Inhibition of MIF tautomerase activity by the test compounds is determined by inhibition of the de-colorization of the assay mixture, often at the 20 sec time point. $IC_{50}$ values for compounds with MIF tautomerase inhibitory activity, corresponding to the concentration of inhibitor that would inhibit MIF tautomerase activity by 50%, are determined by interpolation of the results from MIF tautomerase assays at several different inhibitor concentrations. These $IC_{50}$ values provide a reasonable correlation between MIF enzymatic inhibitory activity of the test compounds, and inhibition of the biological activity of MIF (see below).

Methods of Treatment and Pharmaceutical Compositions

The MIF tautomerase assay was used in Example 1 shows that certain isoxazoline-containing compounds inhibit MIF enzymatic activity. Example 2 shows that certain isoxazoline-based compounds not only specifically inhibit MIF enzymatic activity (i.e, tautomerase), but also inhibit MIF immunoregulatory activities as measured in assays of MIF biological activity. Finally, Example 3 shows the co-crystallization structure of the MIF:isoxazoline complex, showing that three molecules of the S-isomer only of p-hydroxyphenyl-isoxazoline bind stoichiometrically to the three active sites within the MIF trimer. These X-ray data represent valuable information for predicting the next generation of MIF activity inhibitors.

These data provide a reasonable correlation between the MIF tautomerase enzymatic assay and MIF antagonism in a biological assay. Collectively, these data show that inhibition by a compound in the MIF tautomerase assay is predictive of its potential therapeutic use in inhibiting MIF biological activity.

Accordingly, the present invention provides a method for inactivating enzymatic and biological activity of human MIF comprising contacting the human MIF with a compound, or combination of compounds, having an isoxazoline moiety that forms a stable interaction with at least one amino acid residue of the human MIF. Preferably, the interaction occurs at or near the active site of the tautomease activity of the MIF protein. Preferably, the stable interaction is between the isoxazoline moiety of the isoxazoline-containing compound and the N-terminal proline residue of the human MIF. Preferably the compound is a isoxazoline-containing compound of Formula I, wherein Formula I is:

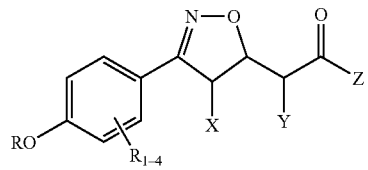

wherein:
$R_{1-4}$ are, independently, R, halo, $N_3$, CN, OH, NRR', or SH;
R and R' are, independently, H or $C_{1-6}$ alkyl;
X is R, halo, $N_3$, CN, OR, NRR', SH, =O, =CH$_2$, or A;
A is a substituted or unsubstituted aromatic ring (substituted, for instance, with one or more groups selected from R, halo, $N_3$, CN, OH, NRR', or SH);
Y is R, NRR', NRR" or (CH$_2$)$_n$-A;
Z is R, OR, OR", NRR', NRR", or A;
R" is a saturated or unsaturated, straight or branched chain $C_2$-$C_{18}$;
and n is 0 or 1.

Preferably, the compound is a p-hydroxyphenyl-isoxazoline-containing compound, wherein each of R, $R_{1-4}$, X and Y is H or —CH$_2$-A, and Z is OR. More preferably, the compound is an ester of (R)-3-(4-hydroxyphenyl)-4,5-dihydro-5-isoxazolineacetic acid, particularly the methyl ester (ISO-1). Still more preferably the compound is and ester of 2-[3-(4-hydroxy-phenyl)-4,5-dihydro-isoxazol-5-yl]-3-phenyl-propanoic acid, particularly the methyl ester (ISO-2).

The present invention also provides a method for treating inflammatory disorders including, but not limited to, arthritis, proliferative vascular disease, ARDS (acute respiratory distress syndrome), cytokine-mediated toxicity, sepsis, septic shock, psoriasis, interleukin-2 toxicity, asthma, MIF-mediated conditions, autoimmune disorders (including, but not limited to, rheumatoid arthritis, insulin-dependent diabetes, multiple sclerosis, graft versus host disease, lupus syndromes), tumor growth or angiogenesis, or any condition characterized by local or systemic MIF release or synthesis, comprising administering an effective amount of a compound of Formula I, wherein Formula I is:

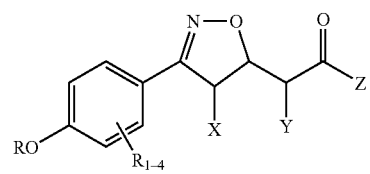

wherein:
$R_{1-4}$ are, independently, R, halo, $N_3$, CN, OH, NRR', or SH;
R and R' are, independently, H or $C_{1-6}$alkyl;
X is R, halo, $N_3$, CN, OR, NRR', SH, =O, =CH$_2$, or A;
A is a substituted or unsubstituted aromatic ring;
Y is R, NRR', NRR" or (CH$_2$)$_n$-A;
Z is R, OR, OR", NRR', NRR", or A;
R" is a saturated or unsaturated, straight or branched chain $C_2$-$C_{18}$;
and n is 0 or 1.

Preferably, the compound is a p-hydroxyphenyl-isoxazoline-containing compound, wherein each of R, $R_{1-4}$, X and Y is H or —CH$_2$-A, and Z is OR. More preferably, the compound is an ester of (R)-3-(4-hydroxyphenyl)-4,5-dihydro-5-isoxazolineacetic acid, particularly the methyl ester (ISO-1). Still more preferably the compound is and ester of 2-[3-(4-hydroxy-phenyl)-4,5-dihydro-isoxazol-5-yl]-3-phenyl-propanoic acid, particularly the methyl ester (ISO-2).

The present invention further provides a pharmaceutical composition comprising a compound having an isoxazoline moiety, or a pharmaceutically acceptable salt thereof, and a pharmaceutically acceptable carrier or diluent, wherein the composition comprises an effective amount of a compound of Formula I, wherein Formula I is:

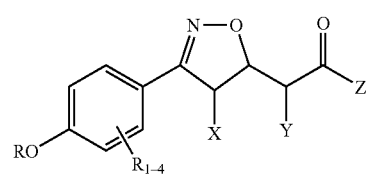

wherein:
$R_{1-4}$ are, independently, R, halo, $N_3$, CN, OH, NRR', or SH;
R and R' are, independently, H or $C_{1-6}$ alkyl;
X is R, halo, $N_3$, CN, OR, NRR', SH, =O, =CH$_2$, or A;
A is a substituted or unsubstituted aromatic ring;

Y is R, NRR', NRR" or $(CH_2)_n$-A;

Z is R, OR, OR", NRR', NRR", or A;

R" is a saturated or unsaturated, straight or branched chain $C_2$-$C_{18}$;

and n is 0 or 1.

with any or all of the following provisos:

(i) when Z=$OCH_3$, at least one of R, $R_{1-4}$, X and Y is not H;

(ii) when R=$R_2$=tert-butyl and each is ortho to OR, at least one of R, $R_3$, $R_4$, X and Y is not H or Z is not $OCH_3$;

(iii) when Z=OH and R=H or methyl, at least one of $R_{1-4}$, X and Y is not H (i.e., the compound is not [3-(4-hydroxy-phenyl)-4,5-dihydro-isoxazol-5-yl]-acetic acid or [3-(4-methoxy-phenyl)-4,5-dihydro-isoxazol-5-yl]-acetic acid ); and (iv) when Z=$OCH_3$, and R=methyl, at least one of $R_{1-4}$, X and Y is not H (i.e., the compound is not [3-(4-methoxy-phenyl)-4,5-dihydro-isoxazol-5-yl]-acetic acid methyl ester).

The present invention further provides a method for treating inflammatory disorders including, but not limited to, arthritis, proliferative vascular disease, ARDS (acute respiratory distress syndrome), cytokine-mediated toxicity, sepsis, septic shock, psoriasis, interleukin-2 toxicity, asthma, MIF-mediated conditions, autoimmune disorders (including, but not limited to, rheumatoid arthritis, insulin-dependent diabetes, multiple sclerosis, graft versus host disease, lupus syndromes), tumor growth or angiogenesis, or any condition characterized by local or systemic MIF release or synthesis, comprising administering an effective amount of a compound having an isoxazoline moiety, wherein the isoxazoline moiety forms a stable covalent interaction with at least one amino acid residue of an MIF protein. Preferably, the interaction occurs at or near the active site of the tautomease activity of the MIF protein. Preferably, the compound is a isoxazoline-containing compound or an hydroxyphenyl-isoxazoline -containing compound. More preferably, the compound is an ester of (R)-3-(4-hydroxyphenyl)-4,5-dihydro-5-isoxazolineacetic acid, particularly the methyl ester (ISO-1). Still more preferably the compound is and ester of 2-[3-(4-hydroxy-phenyl)-4,5-dihydro-isoxazol-5-yl]-3-phenyl-propanoic acid, particularly the methyl ester (ISO-2).

The present invention also provides a pharmaceutical composition comprising a compound having a isoxazoline moiety and a pharmaceutically acceptable carrier, wherein the isoxazoline moiety forms a stable covalent interaction with at least one amino acid residue of an MIF protein. Preferably, the interaction occurs at or near the active site of the tautomease activity of the MIF protein. Preferably, the compound is an isoxazoline-containing compound or an hydroxyphenyl-isoxazoline -containing compound. More preferably, the compound is an ester of (R)-3-(4-hydroxyphenyl)-4,5-dihydro-5-isoxazolineacetic acid, particularly the methyl ester (ISO-1). Still more preferably the compound is and ester of 2-[3-(4-hydroxy-phenyl)-4,5-dihydro-isoxazol-5-yl]-3-phenyl-propanoic acid, particularly the methyl ester (ISO-2).

As an example of the methods of treatment of the present invention, isoxazoline-containing compounds of the present invention can be used to treat patients with ARDS (acute respiratory distress syndrome). ARDS is often considered to be an archetypal clinical response in which the dynamic balance within the immune response shifts toward excessive inflammation and tissue destruction. MIF is expressed in both type II alveolar cells and infiltrating immune cells. MIF levels in the bronchoalveolar lavage of ARDS patients were found to be significantly elevated when compared to control subjects (Donnelly, et al., Nat. Med., 3, 320-323 (1997)). Human MIF enhances both TNFα and IL-8 secretion from ARDS alveolar macrophages (ex vivo) when compared to control cells. Pre-treatment of these cells with anti-MIF antibodies significantly decreases TNFα and IL-8 production from ARDS alveolar cells. Moreover, as discussed above under "Background of the Invention," rMIF (recombinant MIF) was found to override, in a concentration-dependent fashion, glucocorticoid-mediated inhibition of cytokine secretion in ARDS macrophages. These were the first data to indicate that the MIF/glucocorticoid dyad is active in cells that had undergone pro-inflammatory activation in vivo during human disease (Donnelly, et al., Nat. Med., 3, 320-323 (1997). Significantly elevated levels of alveolar MIF were found in those at-risk patients who progressed to ARDS compared to those who did not. MIF likely acts as an important mediator to promote and sustain the pulmonary inflammatory response in ARDS. Its prominent expression in ARDS may explain the fulminant course of this disease and perhaps why glucocorticoid treatment has proven disappointing in established cases. Thus, pharmaceutical compositions comprising isoxazoline-containing compounds of the present invention can be used to treat ARDS patients.

As a further example of the methods of treatment of the present invention, isoxazoline-containing compounds of the present invention can be used to treat patients with rheumatoid arthritis. Synovial fluid obtained from the affected joints of patients with rheumatoid arthritis contain significantly greater levels of MIF than those obtained from patients with osteoarthritis or from normal control subjects (Metz, et al., Adv. Immunol., 66, 197-223 (1997); Leech, et al., Arthritis Rheum., 41, 910-917 (1998); Onodera, et al., Cytokine, 11, 163-167 (1999)). As revealed by immunohistochemical staining methods, infiltrating mononuclear cells within the human arthritic joint are the primary source of MIF. In two animal models of arthritis, neutralizing anti-MIF mAb's significantly inhibited disease progression and disease severity (Leech, et al., Arthritis Rheum., 41, 910-917 (1998); Mikulowska, et al., J. Immunol., 158, 5514-5517 (1997)) giving impetus to the desirability of developing additional MIF inhibitors for potential therapeutic use in inflammatory disease. Thus, pharmaceutical compositions comprising isoxazoline-containing compounds of the present invention can be used to treat arthritis patients.

In yet a further example of the methods of treatment of the present invention, isoxazoline-containing compounds of the present invention can be used to treat patients with atopic dermatits. Atopic dermatitis is a chronic pruritic inflammatory skin disorder. Its pathogenesis, in part, is thought to be due to dysregulated cytokine production by peripheral mononuclear cells. In lesions from patients with atopic dermatitis, MIF protein is diffusely distributed throughout the entire epidermal layer with increased expression by keratinocytes (Shimizu, et al., FEBS Lett., 381, 199-202 (1996)). In normal human skin, MIF has primarily been localized to epidermal ketatinocytes. The serum MIF level of atopic dermatitis patients were 6-fold higher than in control subjects. Additionally, serum MIF levels in atopic dermatitis patients decreased as clinical features improved, suggesting that MIF plays a pivotal role in the inflammatory response in the skin during dermatitis. Thus, pharmaceutical compositions comprising isoxazoline-containing compounds of the present invention can be used to treat patients with atopic dermatitis.

In a similar manner, the present invention also provides a method for treating or preventing other inflammatory or autoimmune disorders including, but not limited to, proliferative vascular disease, cytokine-mediated toxicity, sepsis, septic shock, psoriasis, interleukin-2 toxicity, asthma, MIF-mediated conditions, insulin-dependent diabetes, multiple sclerosis, graft versus host disease, lupus syndromes, and other conditions characterized by local or systemic MIF release or synthesis.

In yet another example of the methods of treatment of the present invention, isoxazoline-containing compounds of the present invention can be used to treat patients with tumor growth. Neutralizing anti-MIF antibodies have been found to significantly reduce growth and vascularization (angiogenesis) of mouse 38C13 B cell lymphoma in vivo (Chesney et al., Mol. Med., 5, 181-191 (1999)). MIF was expressed predominantly in tumor-associated neovasculature. Cultured microvascular endothelial cells, but not 38C13 B cells, were observed both to produce MIF and to require its activity for proliferation in vitro (Takahashi, et al., Mol. Med., 4, 707-714 (1998)). In addition, the administration of anti-MIF antibodies to mice was found to significantly inhibit the neovascularization response elicited by Matrigel implantation, a model of new blood vessel formation in vivo (Bozza, et al., J. Exp. Med., 189, 341-346 (1999)). These data indicate that MIF plays an important role in tumor angiogenesis, a new target for the development of anti-neoplastic agents that inhibit tumor neovascularization.

Thus, the present invention also provides a method for treating or preventing tumor growth or angiogenesis, comprising administering an effective amount of a compound, or combination of compounds, having an isoxazoline moiety and that forms a stable interaction with at least one amino acid residue of an MIF protein. Preferably, the interaction occurs at or near the active site of the tautomease activity of the MIF protein. Preferably, the compound is an isoxazoline-containing compound or an hydroxyphenyl-isoxazoline -containing compound. More preferably, the compound is an ester of (R)-3-(4-hydroxyphenyl)-4,5-dihydro-5-isoxazolineacetic acid, particularly the methyl ester (ISO-1). Still more preferably the compound is and ester of 2-[3-(4-hydroxy-phenyl)-4,5-dihydro-isoxazol-5-yl]-3-phenyl-propanoic acid, particularly the methyl ester (ISO-2).

The present invention also provides a compound of Formula I, or a pharmaceutically acceptable salt thereof, as a pharmaceutical composition comprising either of the aforesaid, for use in a medicine or for the manufacture of a medicament for the treatment or prevention of inflammatory disorders including arthritis, proliferative vascular disease, ARDS, cytokine-mediated toxicity, sepsis, septic shock, psoriasis, interleukin-2 toxicity, asthma, MIF-mediated conditions, autoimmune disorders (including, but not limited to, rheumatoid arthritis, insulin-dependent diabetes, multiple sclerosis, graft versus host disease, lupus syndromes), tumor growth or angiogenesis, or any condition characterized by local or systemic MIF release or synthesis.

Pharmaceutical Formulations

The compounds of the present invention have utility in pharmacological compositions for the treatment and prevention of many diseases and disorders characterized by an MIF response, whereby MIF is released from cellular sources and MIF production is enhanced. A compound of the invention can be administered to a human patient by itself or in pharmaceutical compositions where it is mixed with suitable carriers or excipients at doses to treat or ameliorate various conditions characterized by MIF release. A therapeutically effective dose further refers to that amount of the compound sufficient to inhibit MIF tautomerase activity and MIF bioactivity, it being understood that such inhibition may occur at different concentrations such that a person skilled in the art could determine the required dosage of compound to inhibit the target MIF activity. Therapeutically effective doses may be administered alone or as adjunctive therapy in combination with other treatments, such as steroidal or non-steroidal anti-inflammatory agents, or anti-tumor agents. Techniques for the formulation and administration of the compounds of the instant application may be found in *Remington's Pharmaceutical Sciences,* Mack Publishing Co., Easton, Pa., latest addition.

Suitable routes of administration may, for example, include oral, rectal, transmucosal, or intestinal administration; parenteral delivery, including intramuscular, subcutaneous, intramedullary injections, as well as intrathecal, direct intraventricular, intravenous, intraperitoneal, intranasal, or intraocular injections, and optionally in a depot or sustained release formulation.

Furthermore, one may administer a compound of the present invention in a targeted drug delivery system, for example in a liposome.

The pharmaceutical compositions and compounds of the present invention may be manufactured in a manner that is itself known, e.g., by means of conventional mixing, dissolving, dragee-making, levitating, emulsifying, encapsulating, entrapping, or lyophilizing processes. Pharmaceutical compositions for use in accordance with the present invention thus may be formulated in conventional manner using one or more physiologically acceptable carriers comprising excipients and auxiliaries that facilitate processing of the active compounds into preparations, which can be used pharmaceutically. Proper formulation is dependent upon the route of administration chosen.

For injection, the compounds of the invention may be formulated in aqueous solutions, preferably in physiologically compatible buffers, such as Hank's solution, Ringer's solution, or physiological saline buffer. For transmucosal administration, penetrants appropriate to the barrier to be permeated are used in the formulation. Such penetrants are known in the art.

For oral administration, the compounds can be formulated readily by combining the active compounds with pharmaceutically acceptable carriers well known to those in the art. Such carriers enable the compounds of the invention to be formulated as tablets, pills, dragees, capsules, liquids, gels, syrups, slurries, suspensions and the like, for oral ingestion by a patient to be treated. Pharmaceutical preparations for oral use can be obtained by combining the compound with a solid excipient, optionally grinding the resulting mixture, and processing the mixture of granules, after adding suitable auxiliaries, if desired, to obtain tablets or dragee cores. Suitable excipients are, in particular, fillers such as sugars, including lactose, sucrose, mannitol, or sorbitol; cellulose preparations such as, for example, maize starch, wheat starch, rice starch, potato starch, gelatin, gum tragacanth, methyl cellulose, hydroxypropylmethyl-cellulose, sodium carboxymethylcellulose, and/or polyvinylpyrrolidone (PVP). If desired, disintegrating agents may be added, such as the cross-linked polyvinyl pyrrolidone, agar, or alginic acid or a salt thereof such as sodium alginate.

Dragee cores are provided with suitable coatings. For this purpose, concentrated sugar solutions may be used, which may optionally contain gum arabic, talc, polyvinyl pyrrolidone, carbopol gel, polyethylene glycol, and/or titanium dioxide, lacquer solutions, and suitable organic solvents or solvent mixtures. Dyestuffs or pigments may be added to the tablets or dragee coatings for identification or to characterize different combinations of active compound doses.

Pharmaceutical preparations that can be used orally include push-fit capsules made of gelatin, as well as soft, sealed capsules made of gelatin and a plasticizer, such as glycerol or sorbitol. The push-fit capsules can contain the active ingredients in admixture with filler such as lactose, binders such as starches, and/or lubricants such as talc or magnesium stearate and, optionally, stabilizers. In soft capsules, the active compounds may be dissolved or suspended in suitable liquids, such as fatty oils, liquid paraffin, or liquid polyethylene glycols. In addition, stabilizers may be added. All formulations for oral administration should be in dosages suitable for such administration.

For buccal administration, the compositions may take the form of tablets or lozenges formulated in conventional manner.

For administration by inhalation, the compounds for use according to the present invention are conveniently delivered in the form of an aerosol spray presentation from pressurized packs or a nebulizer, with the use of a suitable propellant, e.g., dichlorodifluoromethane, trichlorofluoromethane, dichlorotetrafluoroethane, carbon dioxide or other suitable gas. In the case of a pressurized aerosol the dosage unit may be determined by providing a valve to deliver a metered amount. Capsules and cartridges of e.g., gelatin for use in an inhaler or insufflator may be formulated containing a powder mix of the compound and a suitable powder base such as lactose or starch.

The compounds may be formulated for parenteral administration by injection, e.g., by bolus injection or continuous infusion. Formulations for injection may be presented in unit dosage form, e.g., in ampoules or in multi-dose containers, with an added preservative. The compositions may take such forms as suspensions, solutions or emulsions in oily or aqueous vehicles, and may contain formulatory agents such as suspending, stabilizing and/or dispersing agents.

Pharmaceutical formulations for parenteral administration include aqueous solutions of the active compounds in water-soluble form. Additionally, suspensions of the active compounds may be prepared as appropriate oily injection suspensions. Suitable lipophilic solvents or vehicles include fatty oils such as sesame oil, or synthetic fatty acid esters, such as ethyl oleate or triglycerides, or liposomes. Aqueous injection suspensions may contain substances which increase the viscosity of the suspension, such as sodium carboxymethyl cellulose, sorbitol, or dextran. Optionally, the suspension may also contain suitable stabilizers or agents which increase the solubility of the compounds to allow for the preparation of highly concentrated solutions.

Alternatively, the active ingredient may be in powder form for constitution with a suitable vehicle, e.g., sterile pyrogen-free water, before use.

The compounds may also be formulated in rectal compositions such as suppositories or retention enemas, e.g., containing conventional suppository bases such as cocoa butter or other glycerides.

In addition to the formulations described previously, the compounds may also be formulated as a depot preparation. Such long acting formulations may be administered by implantation (for example subcutaneously or intramuscularly) or by intramuscular injection. Thus, for example, the compounds may be formulated with suitable polymeric or hydrophobic materials (for example as an emulsion in an acceptable oil) or ion exchange resins, or as sparingly soluble derivatives, for example, as a sparingly soluble salt.

Liposomes and emulsions are well known examples of delivery vehicles or carriers for hydrophobic drugs. Certain organic solvents such as dimethylsulfoxide also may be employed, although usually at the cost of greater toxicity.

Additionally, the compounds may be delivered using a sustained-release system, such as semipermeable matrices of solid hydrophobic polymers containing the therapeutic agent. Various forms of sustained-release materials have been established and are well known by those skilled in the art. Sustained-release capsules may, depending on their chemical nature, release the compounds for a few weeks up to over 100 days. Depending on the chemical nature and the biological stability of the therapeutic reagent, additional strategies for protein stabilization may be employed.

The pharmaceutical compositions also may comprise suitable solid- or gel-phase carriers or excipients. Examples of such carriers or excipients include but are not limited to calcium carbonate, calcium phosphate, various sugars, starches, cellulose derivatives, gelatin, and polymers such as polyethylene glycols.

Many of the compounds of the invention identified as inhibitors of MIF activity may be provided as salts with pharmaceutically compatible counterions. Pharmaceutically compatible salts may be formed with many acids, including but not limited to hydrochloric, sulfuric, acetic, lactic, tartaric, malic, succinic, etc.; or bases. Salts tend to be more soluble in aqueous or other protonic solvents than are the corresponding free base forms. Examples of pharmaceutically acceptable salts, carriers or excipients are well known to those skilled in the art and can be found, for example, in *Remington's Pharmaceutical Sciences,* 18th Edition, A. R. Gennaro, Ed., Mack Publishing Co., Easton, Pa. (1990). Such salts include, but are not limited to, sodium, potassium, lithium, calcium, magnesium, iron, zinc, hydrochloride, hydrobromide, hydroiodide, acetate, citrate, tartrate and malate salts, and the like.

Pharmaceutical compositions suitable for use in the present invention include compositions wherein the active ingredients are contained in an effective amount to achieve their intended purpose. More specifically, a therapeutically effective amount means an amount effective to prevent or inhibit development or progression of a disease characterized by MIF release and production in the subject being treated. Determination of the effective amounts is well within the capability of those skilled in the art, especially in light of the detailed disclosure provided herein.

For any compound used in the method of the invention, the therapeutically effective dose can be estimated initially from tautomerase inhibition assays and cell culture assays. Such information can be used to more accurately determine useful doses in humans.

A therapeutically effective dose refers to that amount of the compound that results in a reduction in the development or severity of a disease characterized by MIF release and production. Toxicity and therapeutic efficacy of such compounds can be determined by standard pharmaceutical, pharmacological, and toxicological procedures in cell cultures or experimental animals, e.g., for determining the $LD_{50}$ (the dose lethal to 50% of the population) and the $ED_{50}$ (the dose therapeutically effective in 50% of the population). The dose ratio between toxic and therapeutic effects is the therapeutic index and it can be expressed as the ratio between $LD_{50}$ and $ED_{50}$. Compounds that exhibit high therapeutic indices ($ED_{50} > LD_{50}$ or $ED_{50} \gg LD_{50}$) are preferred. The data obtained from cell culture assays or animal studies can be used in formulating a range of dosage for use in humans. The dosage of such compounds lies preferably within a range of circulating concentrations that include the $ED_{50}$ with little or no toxicity. The dosage may vary within this range depending upon the dosage form employed and the route of administration utilized. The exact formulation, route of administration and dosage can be chosen by the individual physician in view of the patient's condition. (See e.g. Fingl, et al. (1975), in *The Pharmacological Basis of Therapeutics,* Chapter. 1 page 1).

Dosage amount and interval may be adjusted individually to provide plasma levels of the active moiety which are sufficient to maintain the desired modulating effects, or minimal effective concentration (MEC). The MEC will vary for each compound but can be estimated from in vitro data; e.g., the concentration necessary to achieve a 50-90% inhibition of MIF activity. Dosages necessary to achieve the MEC will depend on individual characteristics and route of administration. However, HPLC assays, bioassays or immunoassays can be used to determine plasma concentrations.

Dosage intervals can also be determined using the MEC value. Compounds should be administered using a regimen that maintains plasma levels above the MEC for 10-90% of the time, preferably between 30-90% and most preferably between 50-90%.

In cases of local administration for instance, direct introduction into a target organ or tissue, or selective uptake, the effective local concentration of the drug may not be related to plasma concentration.

The amount of composition administered will, of course, be dependent on the subject being treated, on the subject's weight, on the subject's age, on the severity of the affliction, on the manner of administration, and on the judgment of the prescribing physician.

The compositions may, if desired, be presented in a pack or dispenser device that may contain one or more unit dosage forms containing the active ingredient. The pack may for example comprise metal or plastic foil, such as a blister pack. The pack or dispenser device may be accompanied by instructions for administration. Compositions comprising a compound of the invention formulated in a compatible pharmaceutical carrier may also be prepared, placed in an appropriate container, and labeled for treatment of an indicated condition.

Materials and Methods

Synthesis. In the examples of the syntheses that follow, all reagents and solvents used were purchased at the highest commercial quality. All solvents used were HPLC grade from Fisher. $^1$H (270 MHz) and $^{13}$CNMR (67.5 MHz) NMR spectra were recorded on a JEOL Eclipse 270 spectrometer. Coupling constants were reported in Hertz (Hz), and chemical shifts were reported in parts per million (ppm) relative to tetramethylsilane (TMS, 0.0 ppm) with CDCl$_3$, DMSO or CD$_3$OD as solvent. Thin layer (TLC) and flash column chromatography were performed using Alumina B, F-254 TLC plates from Selecto Scientific and Fisher Scientific Basic alumina Brockman activity I, respectively. The reactions were monitored by TLC and $^1$HNMR and were stopped when the yield of the crude according to $^1$HNMR was 90-95%.

Reagents. Unless otherwise indicated, all chemicals were purchased from Aldrich or Sigma Chemical Companies, and were of the highest grade commercially available. p-hydroxyphenyl-isoxazoline methyl ester was synthesized in three steps as described previously (Xue, et al., J. Med. Chem., 40, 2064-2084 (1997); Wityak et al., J. Med. Chem., 40, 50-60 (1997); Baraldi, et al., Synthesis -Stuttgart—1994, 11, 1158-1162 (1994); Curuzu et al., Collect. Czech. Chem. Commun., 56, 2494-2499 (1991), which can be summarized as follows (FIG. 1): 4-hydroxy benzaldehyde (4.0 g, 32.8 mmol) and hydroxylamine hydrochloride (2.28 g, 32.8 mmol) were dissolved in methanol (100 mL) followed by addition of sodium carbonate (6.95 g, 65.6 mmol). Overnight reaction gave product 2 in 95% yield (4.3 g). Chlorination of the oxime 2 using N-chlorosuccinimide (4.22 g, 31.6 mmol) in DMF (100 mL) quantitatively furnished chlorooxime 3. Compound 3 was then dissolved in THF/water ( 80/20) and treated with 3-butenoate methyl ester (3 g, 24.5 mmol) and sodium carbonate (7.8g, 73.6 mmol). After completion (12 hr), the product was extracted with ethyl acetate and the organic extracts were washed with brine and dried over magnesium sulfate. Flash chromatography afforded the product, 4, in 75% yield (0.42 g). The structure was confirmed by $^1$H- and $^{13}$C-NMR and mass spectroscopy.

Dopachrome methyl ester was prepared similarly to previously published procedures (Bendrat, et al., Biochemistry, 36,15356-15362 (1997); Swope, et al., EMBO J., 17, 3534-3541 (1998)). Briefly, to an aqueous 4 mM solution of L-3, 4-dihydroxyphenylalanine methyl ester was added NaIO$_4$ to a final concentration of 6 mM. The solution was immediately placed on ice. Assays were initiated at a time when the absorbance at 475 nm reached a maximal value, signifying that the limiting reagent, NaIO$_4$, was consumed. Recombinant human and mouse MIF was expressed in *E. coli* and purified as previously reported (Bernhagan, et al., Biochemistry, 33, 14144-14155 (1994).

Treatment of MIF with Inhibitors. MIF samples (procedure A: 0.72 μg/ml in 50 mM sodium phosphate (pH 6.6) containing 20 μg/ml bovine serum albumin; procedure B: 0.72 μg/ml in 50 mM sodium phosphate (pH 6.6) containing fetal bovine serum; procedure C: 0.1-0.6 mg/ml in 50 mM sodium phosphate at pH 6.6) were treated with various concentrations of the inhibitors for 5-20 minutes (exact times are specified in the text of the Examples below) at room temperature. Treated MIF samples were then analyzed for enzyme activity using the dopachrome tautomerase assay. Protein concentrations were determined using the micro BCA assay (Pierce Chemical Co.).

Dopachrome Tautomerase Assays. To a room temperature solution (0.7 ml) of recombinant mouse or human MIF samples (0.72 μg/ml in the specified buffers from procedures A, B, and C above) was added dopachrome methyl ester (0.3 ml at 4 mM, prepared in situ). The sample was immediately monitored for loss in absorbance at 475 nm compared to untreated MIF solutions and to dopachrome methyl ester without the addition of MIF.

MALDI MS Experiments. Samples were run using a Perceptive Voyager DE MALDI MS (DHB matrix) at the University of Washington Department of Biochemistry Mass Spectrometry Laboratory.

EXAMPLE 1

Enzyme Inhibition Studies. This example illustrates the inhibition of the enzymatic activity of human MIF by isoxazolines. The enzymatic tautomerization activity of recombinant human MIF was performed using L-dopachrome methyl ester as a chromogenic substrate (Bendrat, et al., Biochemistry, 36, 15356-15362 (1997)). The tautomerization reaction catalyzed by MIF, as described in detail above, leads to the formation of a dihydroxyindole product which is colorless.

Figure 3:
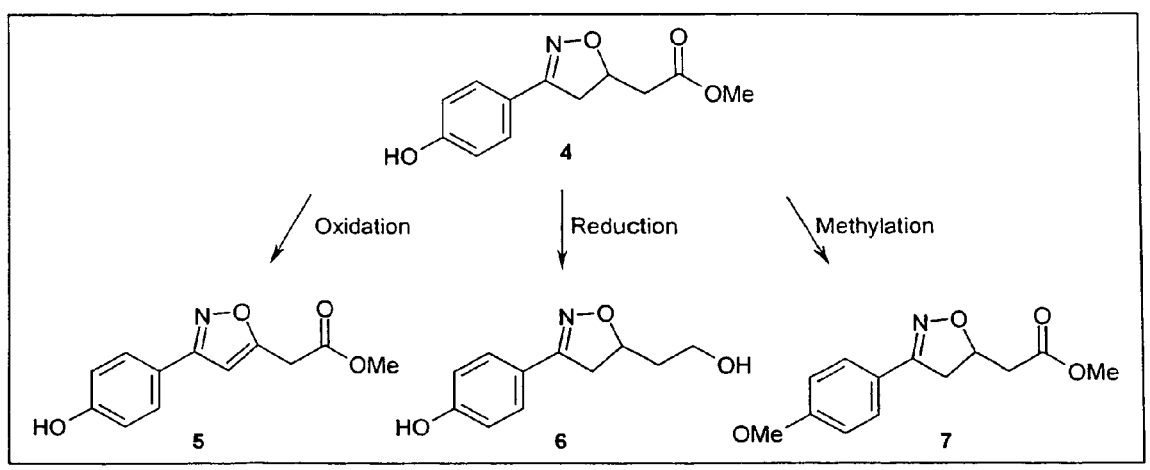
FIG. 3 shows that compound 4 (ISO-1) (FIG. 1) inhibits MIF glucocorticoid regulating activity. The capacity of MIF proteins to regulate glucocorticoid suppression of TNF production in monocytes in the presence of different concentrations of compound 4 was assayed as described previously (Bendrat, et al., Biochemistry, 36, 15356-15362 (1997). The monocytes were purified from peripheral blood by adherence and $1\times10^6$ cells/well pre-incubated for 1 hr with dexamethasone ($10^{-8}$ M), MIF (100 ng/ml native MIF), and/or compound 4 in various concentrations shown in the figure, before the addition of 0.5 µg/ml LPS (E. coli 0111:B4, Sigma Chemical Co.). For the cultures corresponding to the third bar from the left, an amount of solvent (DMSO) equal to that used for solubilization of compound 4 at 20 µM (fifth and sixth bars from left) was added. Cell culture supernatants were collected after 16 hrs and secreted TNFα quantified by a standard, commercially available ELISA. Compound 4 did not affect cell viability, as assessed by MTT reduction by standard methods known in the art. Data shown are mean ±SD of triplicate wells in a representative experiment that was repeated twice, with similar results.

Several isoxazoline derivatives were prepared and tested for activity in the MIF dopachrome tautomerase assay. Compound 4 (FIG. 1) inhibited MIF tautomerase activity in a dose-dependent manner with an IC$_{50}$ of about 10 μM, but the corresponding non-hydroxylated phenyl analog was about 12 times less potent. The 4-methoxy analog (7; FIG. 3) showed no activity, reinforcing an earlier conclusion that a para hydroxyl function is an important feature of our emerging pharmacophore for MIF tautomerase inhibitors, probably attributable to the advantageous formation of a hydrogen bond with Asp97 as suggested by the MIF:phenylpyruvate co-crystalization data.

Figure 2:
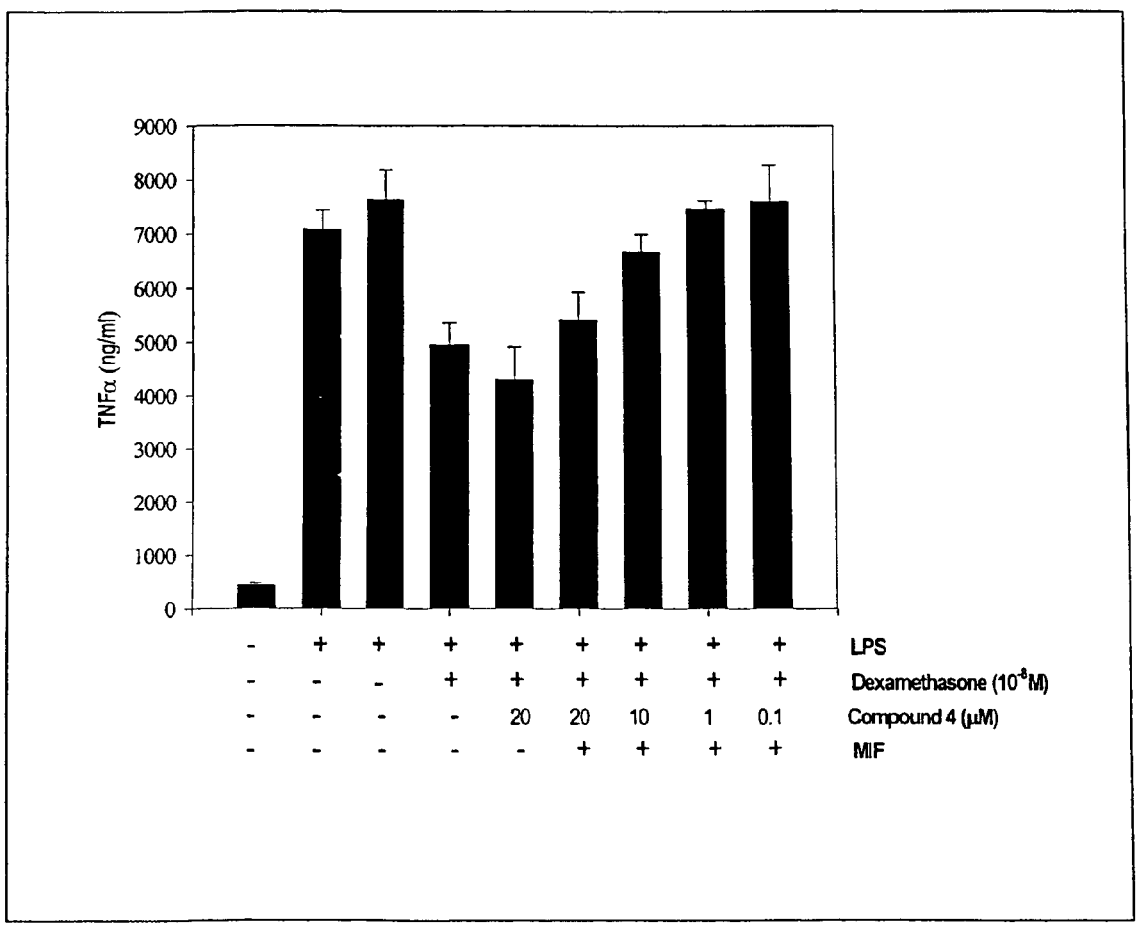
FIG. 2 shows modifications of isoxazoline 4 (ISO-1), including oxidation, reduction and methylation.

To continue structure:activity relationship (SAR) testing in the isoxazoline series, the isoxazoline test compound 4 was oxidized to isoxazole 5 (Xue, et al., J. Med. Chem., 40, 2064-2084 (1997)), as shown in FIG. 2, which eliminated the chiral center, offering a solution to the problem of enantiomeric preference in the isoxazoline series. Surprisingly, the isoxazole 5 was totally inactive in the dopachrome tautomerization assay. As shown in X-ray studies of a crystalline co-structure of MIF and racemic mixture of compound 4, that only the S stereoisomer binds to MIF. To purify the stereoisomers, the enantiomers are conveniently isolated by a chiral separation process using HPLC (Wityak, et al., J. Med. Chem., 40, 50-60 (1997)).

Functionalized Isoxazolines. This section describes a new strategy that aims at improving the binding of the p-hydroxyphenyl ring to the active site of MIF. The new synthesis is begun with either mono- or multi-substitution of the p-hydroxybenzaldehyde ring with group(s) such as —OH, —SH, —CN, —NHAc, —$N_3$ and halides. Initially, structural activity relationships are created at positions 2, 3, 5, and 6 utilizing only commercially available material to synthesize isoxaline derivatives. Synthesis of any starting material needed to serve this aim is conveniently done after close examination of the first set of isoxazoline analogs by measuring the MIF tautomerase activity, as described above..

Figure 4:
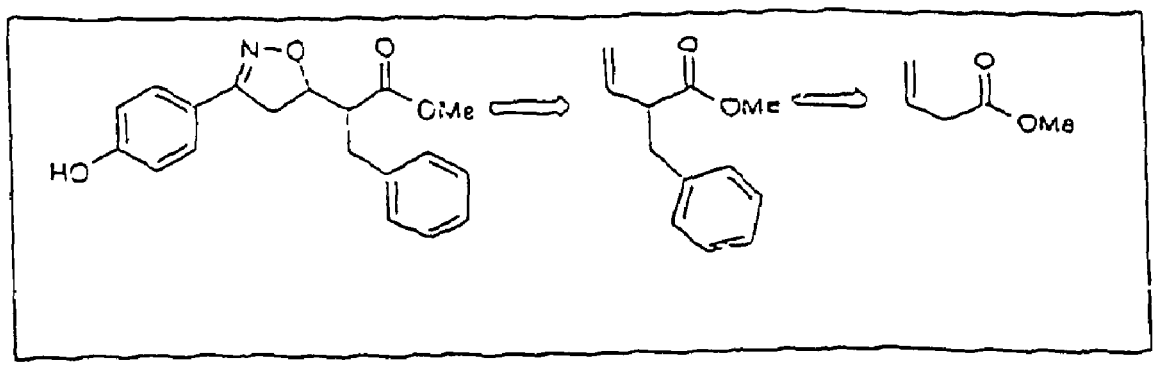
FIG. 4 shows a retrosynthetic approach to 2-[3-(4-hydroxy-phenyl)-4,5-dihydro-isoxazol-5-yl]-3-phenyl-propanoic acid methyl ester (ISO-2).

In previous experience with amino acid Schiff base-type compounds described previously (see U.S. application Ser. No. 09/699,258, supra), the side chain of the amino acid residues played an important roll in improving the binding affinity in the vicinity of the hydrophobic core, by an unidentified mechanism. For instance, in the dopachrome tautomerization assay, the $IC_{50}$ of glycine and tryptophan Schiff base derivatives is 100 μM and 1.6 μM respectively. Initially, a logical approach to improve potency of compound 4 (ISO-1) is functionalization at the alpha position to produce a wide diversity of novel compounds. An initial compound has been synthesized, namely, 2-[3-(4-hydroxy-phenyl)-4,5-dihydroisoxazol-5-yl]-3-phenyl -propanoic acid methyl ester (ISO-2), as a mixture of four diastereomers. Upon fractionation, one fraction, a mixture of two isomers, was found to inhibit MIF dopachrome tautomerase activity with an $IC_{50}$ 550 nM (FIG. 4). However, this synthetic route requires preparation of functionalized alkenes as starting materials (not available commercially) and produces a mixture of four diastereomers. This direct approach therefore requires chiral HPLC separation and, therefore, is less preferred than the above approach of studying structural activity relationships at positions 2, 3, 5, and 6 utilizing only commercially available material to synthesize isoxaline derivatives.

Figure 5:
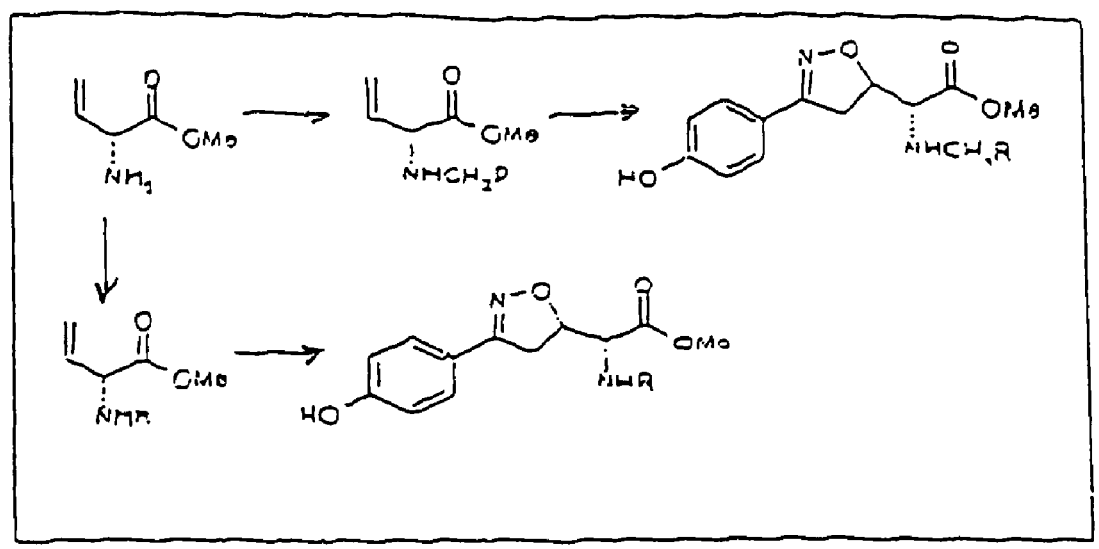
FIG. 5 shows synthesis of functionalized isoxazoline derivatives.

Another approach to functional derivatives of compound 4 begins with pure enantiomer and can be summarized as shown in FIG. 5. This approach provides diversity around the amino functional group and also produces a separable mixture of two diastereomers. This strategy is achieved by starting from R- or S-vinylglycine, both of which are commercially available. Functionalization of each isomer is accomplished by either reductive amidation using a wide range of aliphatic or aromatic aldehydes, or by amidation via coupling with aliphatic or aromatic acid. Moreover, Pd-mediating aryl halides coupling to produce aryl amines also are used in this approach. This approach generates diversity around the amino functions and is based on similar synthetic routes that are well known in the art.

Thus, according to the present invention, the isoxazoline-based compounds related in structure to compound 4 comprise a new and general class of low molecular weight, specific inhibitors of MIF enzymatic activity.

EXAMPLE 2

Biological Assay of MIF Activity. This example shows that isoxazoline-based compounds not only specifically inhibit MIF enzymatic activity, but also inhibit MIF immunoregulatory activities, specifically, MIF glucocorticoid regulating activity. The ability of p-hydroxyphenylisoxazoline methyl ester to neutralize the effect of MIF to influence the anti-inflammatory effect of dexamethasone on TNFα production by human monocytes was tested. As shown in FIG. 3, p-hydroxyphenylisoxazoline methyl ester significantly inhibited the MIF-dependent interference with glucocorticoids in this test system. This property of isoxazoline was dose dependent with an $IC_{50}$ of 5 μM. To address the specificity of this inhibitory effect on MIF, other isoxazoline analogs were tested (e.g., non-hydroxylated form and compounds 5, 6 and 7) that are not such potent inhibitors of MIF tautomerase activity and found that these compounds do not provide any anti-inflammatory activity ($IC_{50}$>100 μM for all), in contrast to the isoxazoline compound 4. These results are consistent with a hypothesis that the pro-inflammatory effects of MIF can be neutralized by the binding of a small molecule at the tautomerase active site, although this effect is not believed to depend on the neutralization of tautomerase activity per se.

The compounds are additionally assessed for inhibition of MIF biological activities in any of a number of assays for MIF biological activity including, for example, inhibition of MIF binding to target cells, inhibition of MIF release or synthesis, inhibition of MIF immunoreactivity with MIF-specific antibodies, alterations of MIF conformation or structural integrity as assessed by circular dichroism spectroscopy, liquid NMR-spectroscopy, X-ray crystallography, thermal stability measurement, inhibition of the pro-proliferative effects of MIF on quiescent NIH/3T3 cells and inhibition of the associated prolonged ERK activation therein, inhibition of MIF-induced arachadonic acid release from NIH/3T3 cells, inhibition of MIF-induced fructose 2,6 bisphosphate formation in L6 myocytes, inhibition of MIF toxicity in the MIF, TNF, or LPS-challenged test animals, inhibition of the glucocorticoid counter-regulatory activity of MIF in vitro or in vivo, inhibition of the MIF-induced functional inactivation of the p53 tumor suppressor protein (Hudson, et al., J. Exp. Med., 190, 1375-1382 (1999), inhibition of MIF-induced release of prostaglandin E2, and inhibition of morbidity or mortality in any of a number of animal models of human diseases that are characterized by the release, production and/or appearance of MIF.

EXAMPLE 3

Co-crystal structure analysis of MIF: isoxazoline 4 (ISO-1). Recently, the crystal structure of MIF complexed with p-hydroxyphenylisoxazoline 4 has been resolved. Similarly to p-hydroxyphenylpyruvate (Lubetsky, et al., Biochemistry, 38,7346-7354 (1999)) and (E)-2-fluoro-p-hydroxycinnamate (Taylor, et al., Biochemistry, 38, 7444-7452 (1999)) co-crytalization with MIF, three molecules of isoxazoline bind each MIF trimer molecule and lie at each interface between two subunits. The inhibitor interacts with Pro-1 and Lys-32 from one subunit and Asn-97 from the adjacent unit.

In particular, the inhibitor 4 interacts with Pro-1 of MIF via the C3 carbon of the isoxazoline ring.

Structural analysis of the bound molecules revealed that only the S-isomer can bind to the MIF cleft, supporting earlier indications that there were likely to be substantial enantiomeric effects in some racemic mixtures of possible inhibitor compounds. Moreover, reduction of the carboxylate moiety of p-hydroxyphenylisoxazoline to furnish the alcohol adduct 6 abolishes the inhibitory effect on the tautomerase activity in an agreement with the postulated importance of this group to form hydrogen bonds with Lys-32.

What is claimed is:

1. A method for inhibiting MIF activity, comprising administering to a subject an effective amount of a compound of Formula I, wherein Formula I is:

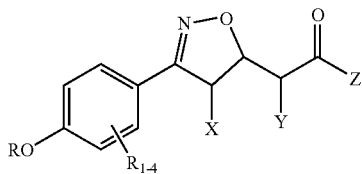

wherein:
- $R_{1-4}$ are, independently, R, halo, $N_3$, CN, OH, NRR', or SH;
- R and R' are, independently, H or $C_{1-6}$alkyl;
- X is R, halo, $N_3$, CN, OR, NRR', SH, =O, =$CH_2$, or A;
- A is an unsubstituted aromatic ring, or an aromatic ring substituted with at least one member selected from the group consisting of R, halo, $N_3$, CN, OH, NRR' and SH;
- Y is R, NRR', NRR'' or $(CH_2)_n$-A;
- Z is R, OR, OR'', NRR', NRR'', or A;
- R'' is a saturated or unsaturated, straight or branched chain $C_2$-$C_{18}$;
- and n is 0 or 1.

2. The method of claim 1, wherein said compound is an ester of (R)-3-(4-hydroxyphenyl)-4,5-dihydro-5-isoxazolineacetic acid.

3. The method of claim 1, wherein said compound is (R)-3-(4-hydroxyphenyl)-4,5-dihydro-5-isoxazolineacetic acid methyl ester.

4. The method of claim 1, wherein said compound is an ester of 2-[3-(4-hydroxy-phenyl)-4,5-dihydro-isoxazol-5-yl]-3-phenyl-propanoic acid.

5. The method of claim 1, wherein said compound is 2-[3-(4-hydroxy-phenyl)-4,5-dihydro-isoxazol-5-yl]-3-phenyl-propanoic acid methyl ester.

* * * * *